United States Patent [19]
Pierfitte et al.

[11] Patent Number: 5,534,701
[45] Date of Patent: Jul. 9, 1996

[54] TOMOGRAPHIC ACQUISITION METHOD HAVING TWO DETECTORS WITH SIGHTING CENTER DISTINCT FROM THE CENTER OF ROTATION

[75] Inventors: Michel Pierfitte, Villepreux; Pierre DeLorme, Voisins les Brettoneux, both of France

[73] Assignee: Sopha Medical, Paris, France

[21] Appl. No.: 152,286

[22] Filed: Nov. 12, 1993

Related U.S. Application Data

[63] Continuation of Ser. No. 894,359, Jun. 4, 1992.

[30] Foreign Application Priority Data

Jun. 7, 1991 [FR] France .................... 91 06962

[51] Int. Cl.⁶ .................................................. G01T 1/166
[52] U.S. Cl. ................. 250/363.04; 250/363.05; 250/363.1
[58] Field of Search .............. 250/363.04, 363.05, 250/363.08, 363.1

[56] References Cited

U.S. PATENT DOCUMENTS

| | | |
|---|---|---|
| 4,652,759 | 3/1987 | Platz . |
| 4,692,625 | 9/1987 | Hanz et al. . |
| 5,105,086 | 4/1992 | Pierfitte et al. .................. 250/363.08 |

FOREIGN PATENT DOCUMENTS

| | | | |
|---|---|---|---|
| 0266846 | 5/1988 | European Pat. Off. . | |
| 250881 | 10/1989 | Japan ............................. | 250/363.04 |

Primary Examiner—Carolyn E. Fields
Attorney, Agent, or Firm—Robert Groover; Betty Formby

[57] ABSTRACT

To acquire measurement data elements during a tomography type experiment in nuclear medecine, with a gamma camera having two detector heads, each of these heads is oriented on a sighting center P while the set of two heads rotates about a center of rotation Ia of the apparatus, the center of rotation being offset from the sighting center. It is shown that this approach provides speedier operation for the acquisition and also contributes to the preparation of tomography images that are more precise and more easily computed.

18 Claims, 5 Drawing Sheets

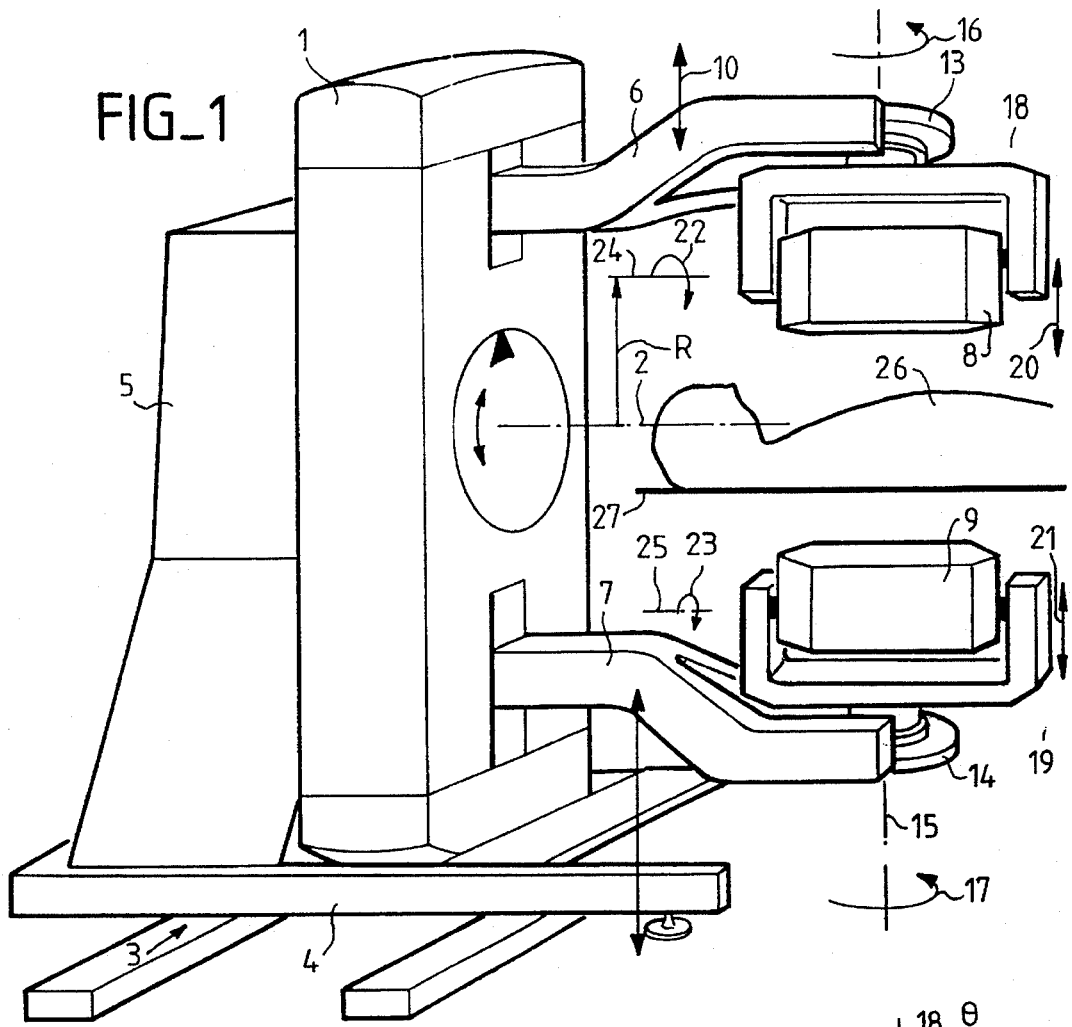
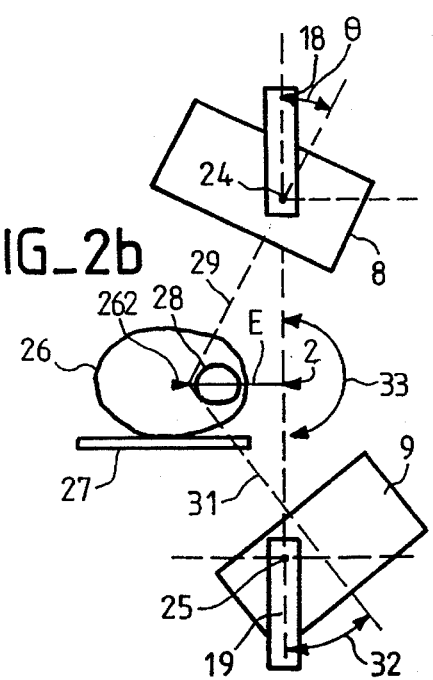
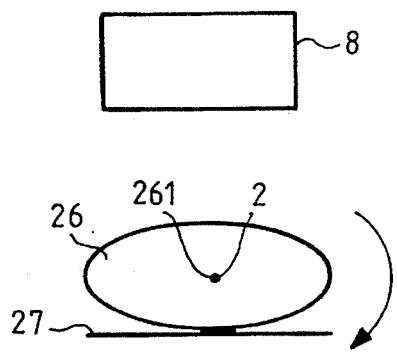
FIG_2a PRIOR ART

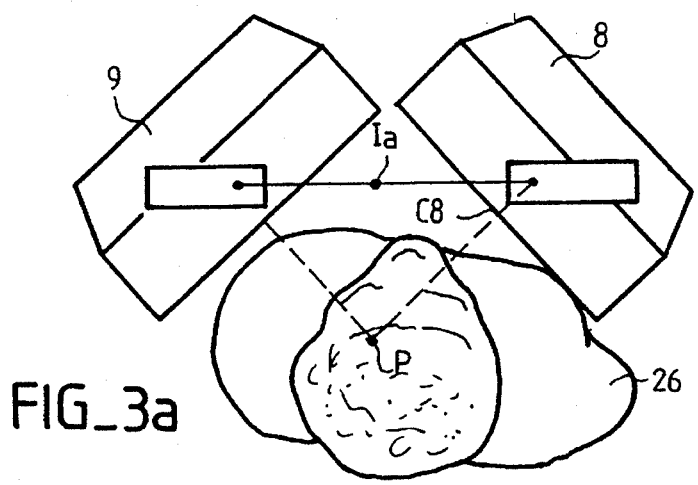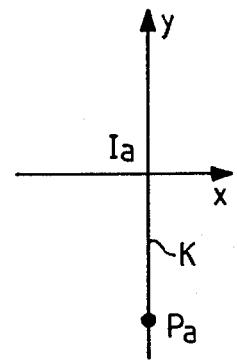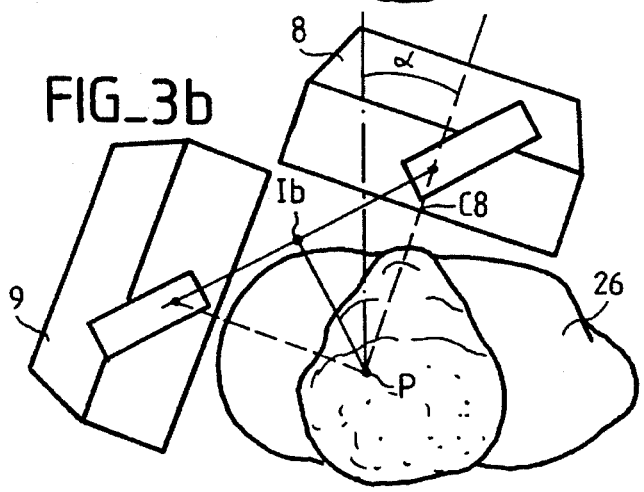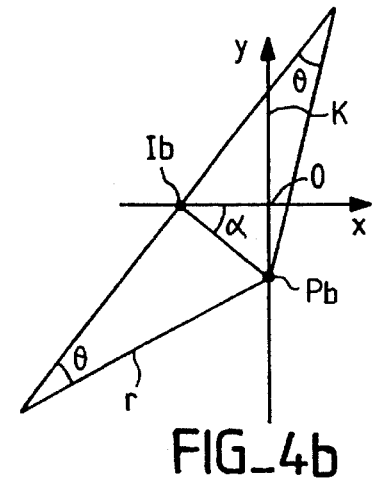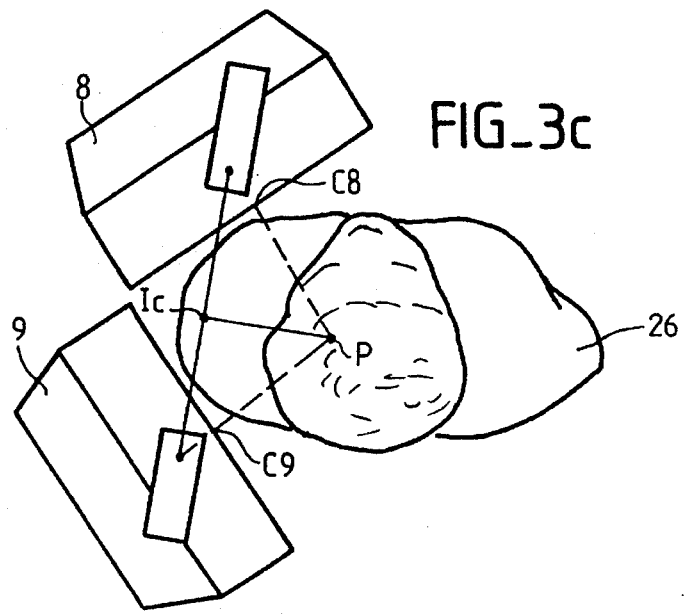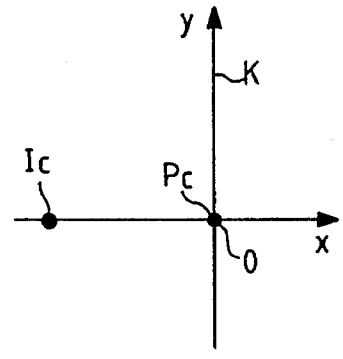

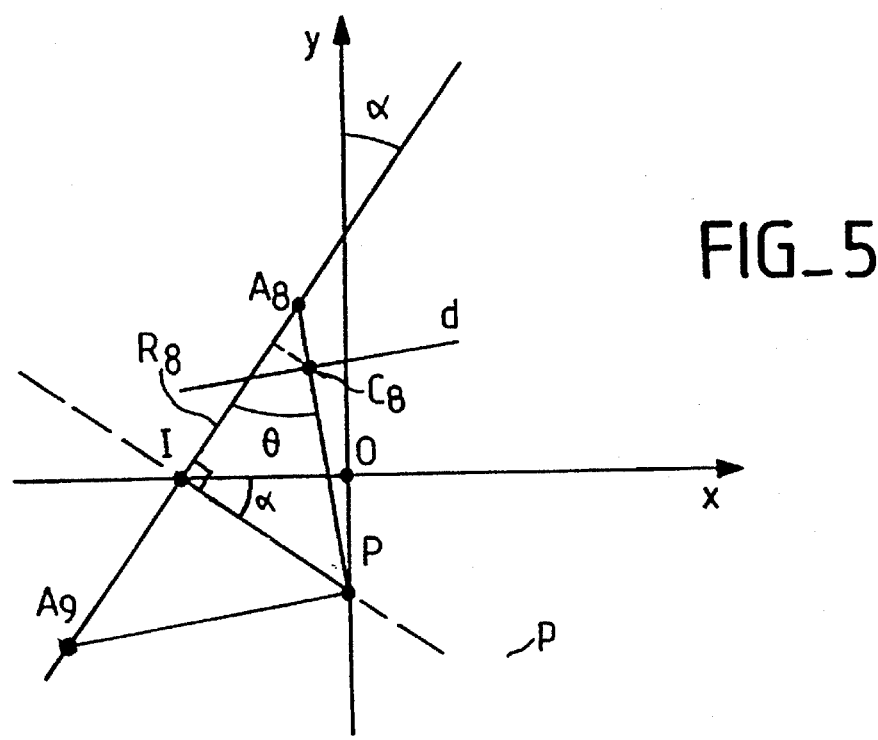
FIG_5
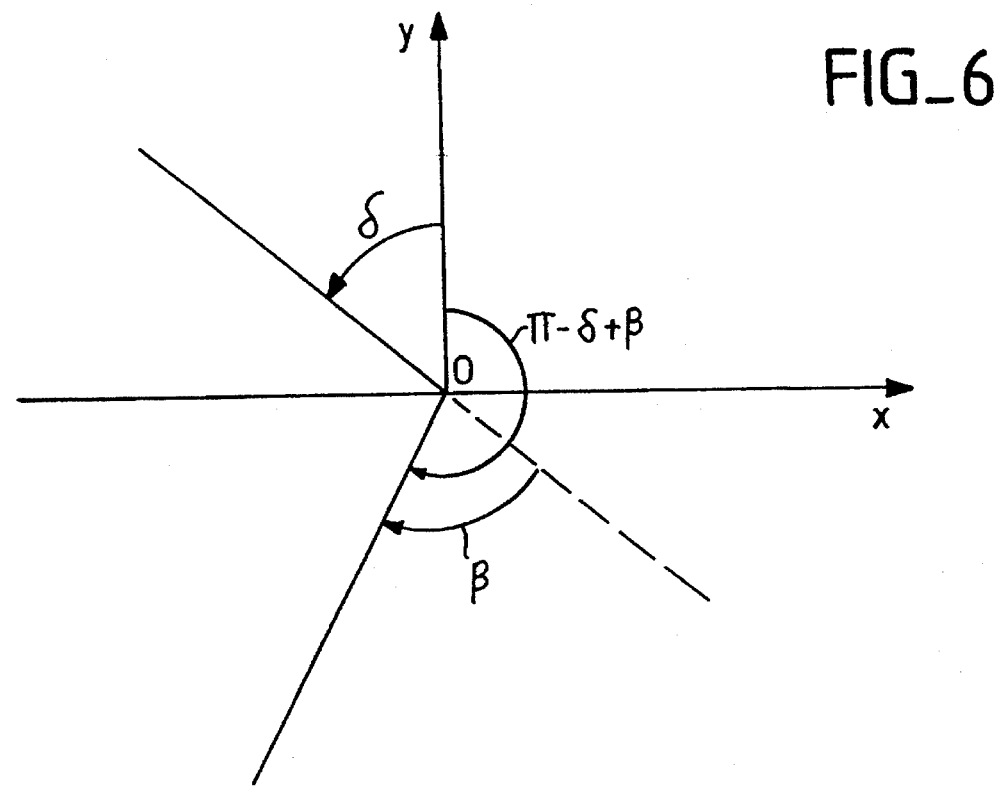
FIG_6

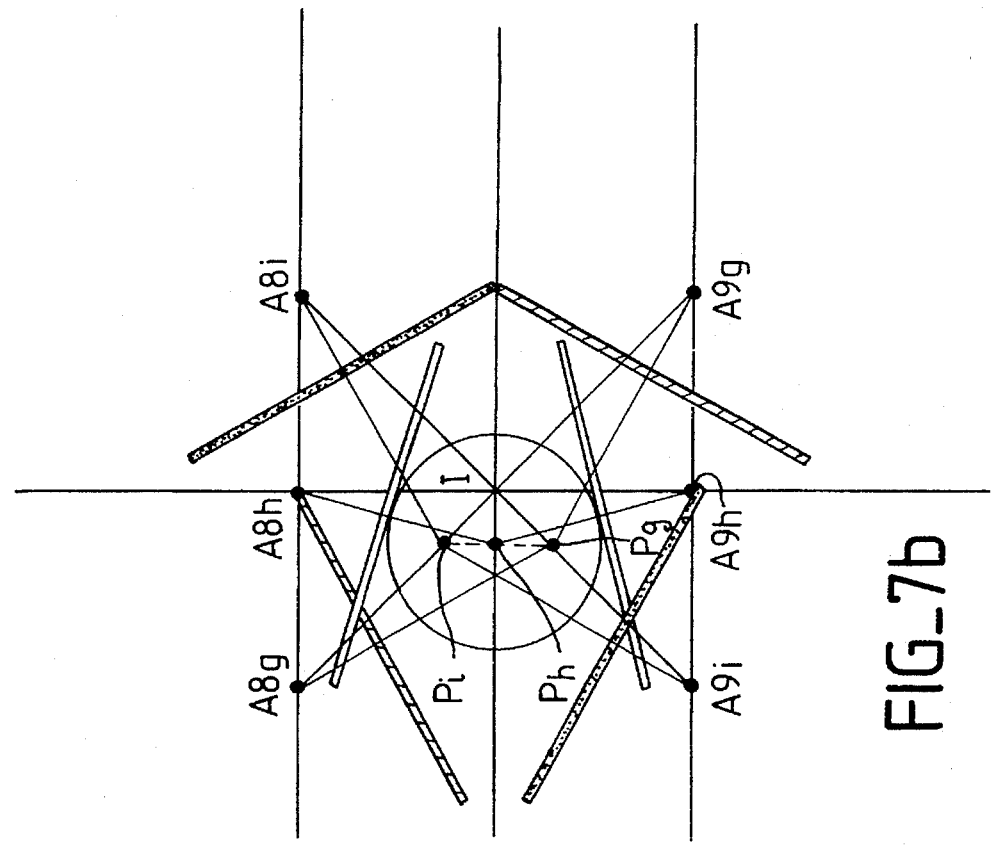
FIG_7b
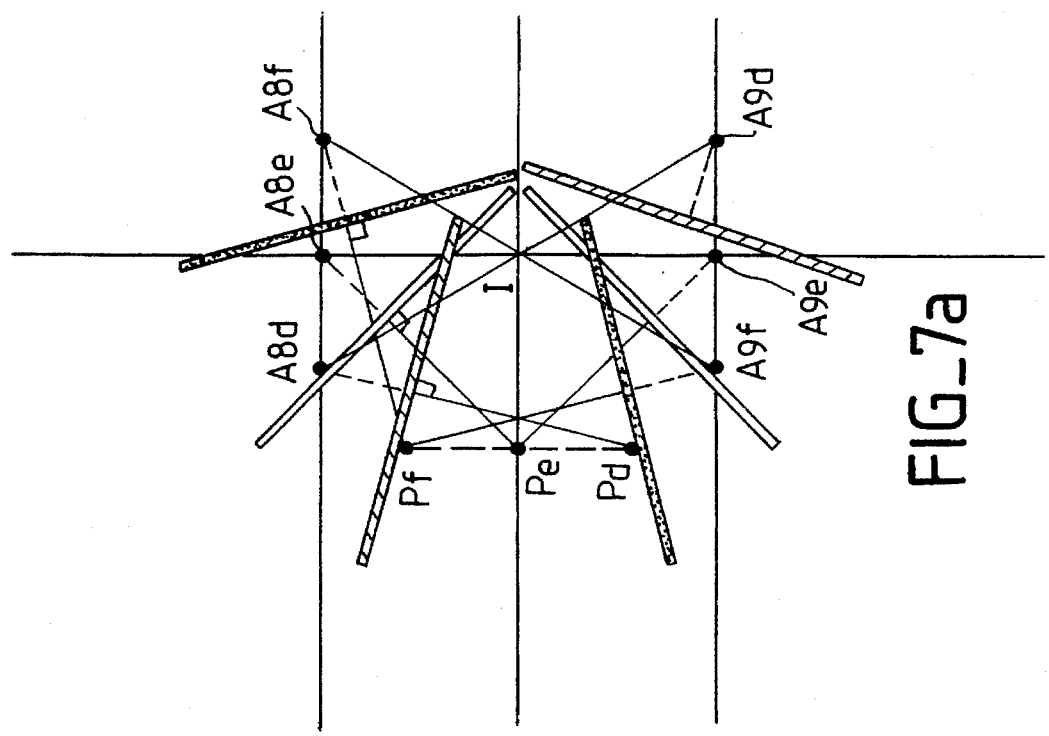
FIG_7a

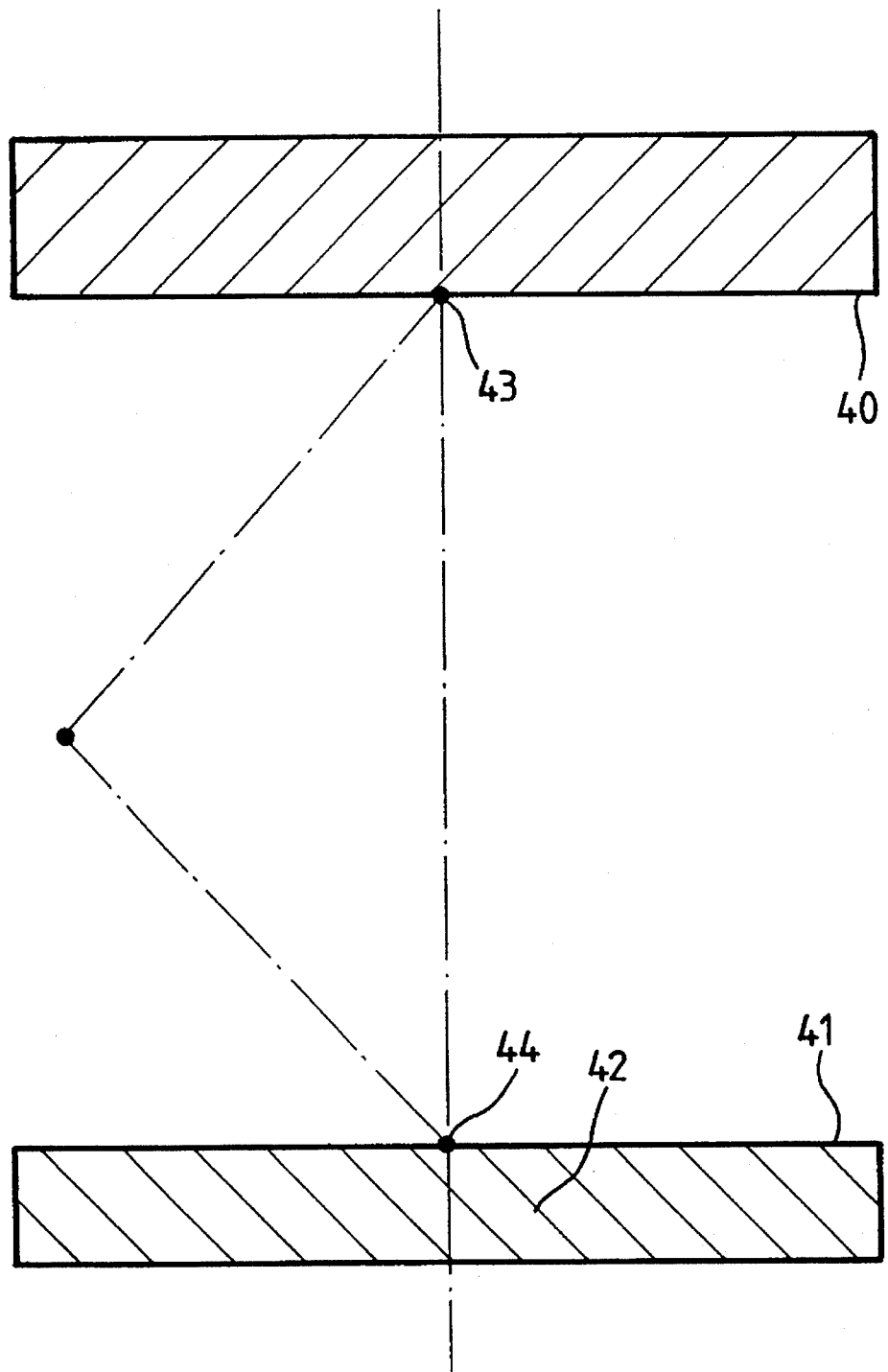
FIG_8

TOMOGRAPHIC ACQUISITION METHOD HAVING TWO DETECTORS WITH SIGHTING CENTER DISTINCT FROM THE CENTER OF ROTATION

This is a continuation of application Ser. No. 07/894,359, filed Jun. 4, 1992.

BACKGROUND OF THE INVENTION

1. Field of the Invention

An object of the present invention is a method for the acquisition of images with a gamma camera during a tomographic examination in nuclear medicine.

The invention is especially promising when the self-attenuation of the gamma rays in the patient is high: in particular for myocardial tomography, hence for organs located on the side of the human body. However, this in no way restricts the invention to this type of use.

2. Description of the Prior Art

Gamma cameras are described, for example, in the U.S. patent by Anger, U.S. Pat. No. 3,011,057. A gamma camera is an apparatus comprising a stand, which is rotating, fixed or movable with respect to the ground and carries a detector, also called a detector head, at the end of an arm. This detector is provided with an array of photomultiplier tubes, the input faces of which are juxtaposed with one another and constitute the detection surface of the detector head and its detection field.

The following is the principle of the examination. A radioactive substance is injected into a patient to be examined. This substance is, for example, thallium for the examination of the myocardium. The radioactive emission excites a scintillator crystal of the detector which converts the energy of the gamma photons into a light energy that can be detected by the photomultiplier tubes. The scintillator crystal is preceded, in a standard way, by a collimator defining a sighting direction and characterized by a focal point. This focal point is pushed back to infinity in the case of collimators with parallel, straight or inclined holes. The focal point is at a finite distance, which is positive or negative, in the case of convergent or divergent collimators. The focal point may be off-centered with respect to a central sighting direction.

The scintillations emitted are detected by the photomultiplier tubes which produce electrical signals depending on the light intensity received. By carrying out barycentric tracking operations on all these electrical signals, it is possible, in a known way, to determine the localization X Y of the origin of the scintillation in the detection field. An incremental acquisition is then carried out by totalizing the number of scintillations (or strokes) detected per localization element called a pixel.

By leaving the detector head in a given position for a certain time above the examined body, it is then possible, for a given angle of sight, called a projection, to obtain an image that reveals the concentration of the emitting substance in the body. A tomographic examination consists in acquiring one image per angle of sight, for a large number of angles of sight, evenly spaced out on an angular sector of at least 180°. It is then possible, with computation algorithms, notably filtered back projection, to reconstitute the image of a volume of the body.

For cardiac applications, given the movement of the heart, the procedure furthermore entails a synchronization of acquisitions. To increase the sensitivity of the camera, the common practice has been to use a rotating stand provided with two detector head instead of only one. These two heads face each other and rotate, together, about the patient being examined. They both contribute to the acquisition of the projections. The sighting directions of the two detectors then coincide. They go through the rotation axis of the system.

This type of geometry does not improve the sensitivity for cardiac examinations because of the following reasons. The attenuation is all the greater as the energy of the isotope used is low. As a consequence, the projections of the 180° angular sector acquired (which gives the nearest projection of the organ to be studied and minimises the self-attenuation of the tissues interposed between this organ and the detector) are far more significant than the projections of the opposite angular sector. Furthermore, the use, if any, of the opposite sector during the filtered back projection lowers the value of the result obtained. It thus appears that the second detector is unnecessary in this case.

This drawback, moreover, is also found with three-head or four-head gamma cameras, for which there are always one or two unnecessary detector heads.

It is an object of the invention to overcome the drawbacks mentioned by proposing, with a two-head camera, a camera geometry and kinematic parameters of examination that are different so as to double the sensitivity. The principle of the invention consists in off-setting the sighting center, defined as the intersection of the two sighting directions, with respect to the axis of rotation of the gamma camera. This may be obtained, for example, in two ways. In a preferred way, the detection fields of the two detector heads are no longer parallel. This geometry is obtained by (preferably) symmetrical angular rotations or "angulations" of the detector heads with respect to the horizontal plane passing through the rotation axis of the stand while this stand is in a vertical orientation. In another way, collimators with inclined holes make it possible to obtain the offsetting of the sighting center with respect to the axis of rotation, while the detection fields may remain parallel. In this case, it is necessary to have as many collimators as there are possible offset values. Naturally, it is possible to associate the two techniques and obtain the chosen offset, by the angulation of the heads on the one hand and by providing the detectors with inclined hole collimators on the other.

It is then shown that the rotation angle about the body can be divided by two. In particular, in a preferred variant of the invention, when the angulation of the detectors or the sighting direction of the collimators is equal to 45°, the 180° tomographic acquisition is obtained by a rotation of the stand of only 90°. The patient supporting element is then driven by an ascending motion while the stand is driven by a motion of lateral translation (or vice versa), in synchronism with the rotation of the detectors. The relative motion of the patient with respect to the stand or of the stand with respect to the patient being an arc of a circle.

SUMMARY OF THE INVENTION

An object of the invention is a method for the acquisition of tomographic images, in the course of an examination in nuclear medicine, carried out with a gamma camera with two detector heads, these two heads being held in a position facing each other by a stand rotating about a rotation axis, wherein:

each of the two heads is provided with an axis of angulation of its sighting direction, these two angulation axes being parallel to the axis of rotation of the stand, this axis of rotation of the stand being contained in the plane defined by these two axes of angulation;

the sighting direction of each of the heads is oriented in angulation, thus defining a sighting center having an offset with respect to this axis of rotation.

BRIEF DESCRIPTION OF THE DRAWINGS

The invention will be understood more clearly from the following description and from the accompanying figures. These are given purely by way of an indication and in no way restrict the scope of the invention. Of these figures:

FIG. 1 shows a two-head gamma camera to implement the method of the invention;

FIGS. 2a and 2b are comparative schematic drawings of acquisition methods in the prior art and in the invention respectively;

FIGS. 3a to 3c and 4a to 4c are drawings of different positions of the set of detector heads in a preferred variant of implementation of the invented method;

FIGS. 5 and 6 are geometrical diagrams that can be used to explain the kinematic parameters of the shifting of the heads during a tomography;

FIGS. 7a and 7b are geometrical diagrams showing a variant of implementation of the method of the invention.

FIG. 8 shows an alternative embodiment with inclined holes in the collimators.

MORE DETAILED DESCRIPTION

FIG. 1 shows a gamma camera that can be used to implement the method of the invention. This gamma camera has a rotating stand 1 capable of rotating about an axis of rotation 2 owing to the fact that it is held rotationally on an underframe 3 provided with footing 4 and a supporting frame 5. This movement shall be called rotation in the rest of the description. The stand 1 has two carrier arms, 6 and 7, each carrying a detector head 8 and 9 respectively of the gamma camera. In a known way, these arms can move away from or towards each other, symmetrically, in the direction of the double-headed arrow 10 by a mechanism of radial movement contained within the stand 1 and, furthermore, motor-driven by electrical motors.

Each arm 6 and 7 has a ring, 13 and 14 respectively, at its end. To each of the rings 13 and 14, there is fixed a stirrup 18 and 19. The two flanks of each of these stirrups comprises a mechanism capable firstly of permitting a telescopic movement, in the direction indicated by the arrows 20 and 21, of the detector heads 8 and 9 as well as a rotation, hereinafter called an "an angulation", 22 and 23 respectively, about the axes 24 and 25 of the detector heads. These movements are, moreover, described in another patent application filed on the same date by the present Applicant. The angulation axes pass directly over the middle of the detection field of each of these heads. They are parallel to these fields. The telescopic movement enables each of the heads 8 and 9 to be shifted independently (and no longer symmetrically as with the radial movement 10 of the arms 6 and 7). When the angulation axes are at the end of the stirrups 18 and 19, these detector heads may under go a +90° or −90° angulation movement 22 or 23. In the method of the invention, it will be seen that the angulation chosen is preferably one of 30° to 45° for a tomographic acquisition with the best possible data, but can range from 5° to 75° in down-graded modes. Room is then left for carrying out a telescopic movement.

In one example, the detector heads have a rectangular detection field. The big length of this rectangle is parallel to the angulation axis 24.

The telescopic and rotational movements are preferably motor-driven by electrical motors. The angulation movements are done manually with the possibility of selection among pre-defined positions. In one example, these pre-defined positions are constituted by notches made on the periphery of circular plates concentric to the axis of angulation and fixedly joined to each of the heads. Two catches may get engaged in these notches and may thus keep the angulation of the heads in pre-defined positions.

A patient 26 under examination is placed substantially between the two detector heads 8 and 9, on a patient-bearing bed 27.

FIG. 2a gives a schematic view of the principle of the performance of a tomography in the prior art. The two detector heads 8 and 9 are normally placed facing each other, on each side of the patient 26 being examined. The rotation axis 2 of the stand is substantially the same as the sighting center 261. On the contrary, in the invention, as shown in FIG. 2b, the rotation axis 2 is offset by a distance E from the sighting center 262. In particular, for a patient with a heart 28 on the left (this patient is seen herein from the foot side), the rotation axis of the stand is offset to the left of this patient. FIG. 2b also shows the traces plotting the axes 24 and 25 aligned with the trace plotting the rotation axis 2. These three axes are in a same plane. It is seen that the detector head 8 has been rotated in angular rotation or "angulation" and that its main sighting direction 29 goes through the sighting center 262. The angulation θ has a value of about 15° to 45°. The same elements are seen again for the detector head 9 with a sighting direction 31 and an angulation 32. The rotation of the stand is done, as indicated by the arrow 33, about the center of rotation 2.

FIGS. 3a to 3c, 4a to 4c, 5 and 6 shall now be used to show how the invention is implemented in a preferred embodiment. A variant shall be shown by means of FIG. 7. The description of angulations should be understood to include also the alternative use of collimators 40 and 41, as shown in FIG. 8, with inclined holes 42, or even a combination of both approaches. In these cases, the axes of angulation 43 and 44 are understood to be the straight line parallel to the rotation axis and passing through the field middle of the field detector.

The detection fields have dimensions smaller than or equal to those of the detector.

The principle of the preferred embodiment consists in keeping unchanged the geometrical diagram constituted by the sighting center P, the projection I of the rotation axis 2 in the plane of tomographic rotation, and the centers C8 and C9 of the fields of detection of the detectors 8 and 9, while the apparatus rotates about the patient 26. A tomography with constant sighting center P is then obtained. It is possibly, thereby, to expect more strictly accurate results when the images are reconstructed.

FIGS. 3 and 4, referenced a, b and c, show three initial, intermediate and final positions of the apparatus during its exploratory rotation in the preferred embodiment. To obtain this result, the bed is shifted vertically. Thus, as shown in FIGS. 4a to 4c, the position of the point P has passed from a low position Pa to a high position Pc measured with respect to a fixed reference K having a center O. It has passed through an intermediate position Pb. On the contrary, the rotation axis of the stand has gradually shifted laterally leftwards, from its initial position Ia to its final position Ic.

These two movements are known per se, the bed being provided with a raising device and the stand being capable of shifting laterally in sliding with the underframe 3 on rails. The upward movement of the bed is done along the axis Y of the reference K. The lateral shifting of the footing takes place along the axis X of the reference K.

To make it possible to carry out a tomography of the heart, the apparatus is positioned so that the sighting center P is substantially at the center of the patient. A detector head is used to explore an angular sector during the rotation of the stand. The exploration of this sector is complemented by the exploration carried out by the second head. For the reconstruction of the images to be accurate, it is necessary for the two explorations to be continuous or to overlap. Each head should therefore explore at least one angular sector of 90°.

FIG. 5 shows the geometrical diagram referred to further above with, in addition, the angle θ of angulation of a detector head, the detector dimension of which is d, the length of the detection field being smaller. The rotation angle α of the stand is the angle made by the straight line A8IA9 with the axis Y, A8 and A9 being the traces plotting the axes of angulation in the tomographic plane. FIG. 5 makes it possible to calculate the constraints of space requirements and of feasibility of examinations with the method of the invention. To simplify these calculations, it has been chosen to place the sighting center P on the perpendicular p to the straight line going through A8IA9. However, there could be another configuration, notably if the angulations of the two heads are not equal. The reference r designates the distance from the sighting center P to the center of the field C of the detector head. R designates the radius dictated by the stand to move the detector heads apart symmetrically. $R_8$ (or $R_9$) designates the radius proper to the head 8 (or 9). Its value is equal to IA8–A8C8. The position of the point A8 depends on the value of the telescopic movement of the detector 8. In one example, d is equal to 45.2 cm, AC is equal to 13 cm and R ranges from 8 cm. to 35 cm.

To prevent the heads from going into collision, it is necessary, already, for r to be greater than $d/2 \cdot \tan\theta$.

FIG. 6 shows the practical conditions of the acquisitions of the views. For clinical reasons, the start of the exploration is offset by an angle δ with respect to the vertical. The total angle of exploration is equal to at least 180° (to meet the constraints of the reconstruction computations). Besides, it may be desired to exceed the value of 180° by the value of the angle β. In practice δ is equal to 45° and the value of β may be of the order of 60°. Each of the two heads may be subjected to an angulation by a different angle $\theta_1$ and $\theta_2$ respectively. In this case, these two angles are chosen such that their sum is equal to $(\pi-\beta)/2$.

The examination procedure is very simple. The patient lies on the bed. The two heads are placed above him or her (substantially symmetrically on each side of the vertical). And the stand explores a field of at least 90° by rotating to the side on which the organ to be examined is located. For the angular sectors of exploration to be contiguous, it has been computed that β should be greater than π–4.θ. Since, furthermore, beyond β=60°, there is a major self-attenuation which means that it is no longer possible to record useful data, it is deduced, by using the foregoing relationship, that θ should be greater than 30° to have good results. Indeed, the information elements detected by the lower detector head are no longer significant (the radioactive emissions are excessively attenuated towards the right by the presence of the vertebral column). The following values are then found for the angulation angle θ, the added angle of exploration or complement β, the rotation S of the stand:

| θ | β | S |
|---|---|---|
| 45° | 0° | 90° |
| 30° | 60° | 120° |

In both these cases, the examination is swifter because the rotation is smaller than 180°.

It can be written (see FIG. 5) that the lateral offset OI of the rotating stand is equal to OI=IP cosα. Similarly, it can be written that the altitude of the bed is OP=IP sinα. Besides, it is known that IP=IA8 tanθ. This enables the simple writing of all the relationships that link the shifts of the moving parts of the gamma camera during the implementation of the method of the invention. Indeed, the distance IP is the basic datum of the method and remains constant throughout the examination. IP varies from one examination to another as a function of the patient's morphology. The value of this distance IP can be measured preferably as follows;. First of all, θ is set at a chosen value, the two heads being placed at a distance from each other. The gamma camera is then placed in the initial position of the examination to be made. For example, this position is that of FIG. 3a. The heads are then brought closer until the patient is almost touched. The radius can then be measured or known by construction since IAC8 is known. This knowledge can be obtained by a sensor measuring the amplitude of the radial movement. From the knowledge of the radius, the values of IA8 and IP can be deduced by construction. The useful travel of the bed in terms of height and of the stand in terms of lateral shifting are also deduced therefrom. The latter information elements are also used to deduce the constraints that link the relative positions in elevation of the bed and in lateral translation of the rotating stand to the angle α of rotation of this rotating stand. Thus, in the preferred embodiment, θ is equal to 45° (tanθ=1), IP=IA8, the starting angle α is equal to –90°, the final angle α is equal to 0°.

The motor drive systems of these shifts in elevation and in translation are servo-linked with servo systems, the transfer functions of which are the ones indicated here above, taking α as variable and IP as constant.

FIGS. 7a and 7b show variations of the implementation of the method of the invention wherein the stand is not shifted laterally. Only the bed is shown from a low position to a high position during the examination, while the stand rotates on itself. There is then obtained a gain of a movement which does not have to be carried out. In the example of FIG. 7a, each of the heads undergoes an angulation of 45°. While the center of rotation of the stand remains fixed at the point I, the sighting center (corresponding to the center of the patient's body) rises vertically from the position Pd to the position Pe, then Pf. During this movement, the projections in the tomography plane of the axes of angulation of the heads, 8 and 9 successively and respectively occupy the positions A8d to A8f and A9d to A9f. These positions are aligned on two parallel and horizontal straight lines. During this movement, the radius is brought into play, firstly to bring the heads closer to each other symmetrically (from the position d to the position e), then they are moved away (from the position e to the position f). This can be seen in FIG. 7a where, in the positions d and f, the ends of the detectors which are closest: to each other are moved away from each other whereas they come almost into contact in the position e.

This furthermore makes it possible to adjust the heads. Thus, first of all the heads are subjected to an angulation of 90°. Then, they are brought closer together until they almost touch each other, by bringing the radius into play, this being achieved while the stand is vertical. We then know the altitude of the straight lines D8 and D9 on which the angulation axes should get shifted. We deduce the equation of the heightwise shift of the bed and the equation of the variation of the radius as a function of α by a trigonometrical computation. Indeed, in this approach, the product IA.cosα is a constant value. The radius is therefore proportional to 1/cosα.

In FIG. 7b, it has been sought to reduce the heightwise clearance of the bed during the exploration, again by keeping the rotation center I fixed. A low angle of angulation (15°) has been chosen. In this case, the heightwise shift of the bed is small but the variation of the bed is more appreciable. This figure also shows the rotation center I placed in the middle of the segments A8-A9, the segments A8-P and A9-P being perpendicular to the fields of detection of the heads.

To complement these two general approaches (with the stand in a translation movement and the bed in an ascending movement, or the bed alone in an ascending movement), it is indicated that it is moreover possible to prompt a relative shift of the axis of rotation I of the stand in the tomographic plane in a circle with a center P and a radius IP.

Finally, it is possible to carry out another total exploration in which, during the rotation, neither the bed nor the rotation axis of the stand are shifted. With such an acquisition, the physical sighting center is not fixed in the patient's body. It can nevertheless be shown that, in the detection field, it is possible to identify a smaller, sliding detection surface in this field which makes it possible to define a "useful" sighting center that is always fixed. Then, in accordance with the invention, there is always a constant offset between this useful sighting center and the axis of rotation. A constant useful sighting center is obtained by extracting a useful field from the detection field as a function of the rotation angle α.

What is claimed is:

1. A method for the acquisition of tomographic images, in the course of an examination in nuclear medicine, carried out with a gamma camera with two detector heads, these two heads being held in a position facing each other by a stand rotating about a rotation axis, wherein:

at least one of the two heads is provided with an axis of angulation of its sighting direction, this angulation axis being parallel to the axis of rotation of the stand;

the sighting directions of the heads defining a sighting center having an offset with respect to this axis of rotation.

2. A method according to claim 1 wherein the axis of rotation of the stand is circularly shifted relative to said sighting center.

3. A method according to claim 1, wherein the examination is a tomography, wherein a body is explored by making the stand rotate about an axis of rotation, and wherein the sighting center is outside the axis of rotation, in a plane transversal to this axis.

4. A method according to claim 3 wherein:

these two heads are made to rotate together by an angle appreciably smaller than 180 degrees.

5. A method according to claim 3 wherein:

the center of rotation and the sighting center are shifted during the rotation, and wherein the value of the offset is maintained during the rotation.

6. A method according to claim 3, wherein the center of rotation is shifted horizontally while the sighting center is shifted vertically.

7. A method according to claim 1 wherein:

these two heads are made to rotate together by an angle appreciably smaller than 180 degrees.

8. A method according to claim 1 wherein:

the center of rotation and the sighting center are shifted during the rotation, and wherein the value of the offset is maintained during the rotation.

9. A method according to claim 1, wherein the center of rotation is shifted horizontally while the sighting center is shifted vertically.

10. A method according to claim 1, wherein the sighting directions of the two heads are oriented in such a way that their main sighting directions form an angle of 90° with each other.

11. A method according to claim 1, wherein:

the sighting directions of two heads are put out of orientation with an equal angle with respect to basic orientations which they have when these sighting directions are parallel.

12. A method according to claim 1, wherein the two heads are subjected to an angulation with an equal angle with respect to basic orientations which they have when these sighting directions are parallel.

13. A method according to claim 1, wherein each of the two heads is subjected to angulation by an angle of $\theta_1$ and $\theta_2$ respectively, such that the sum of these two angles is equal to $(\pi-\beta)/2$ where $\beta$ is a complementary sector of exploration beyond a main sector of 180°.

14. A method according to claim 1, wherein:

the sighting directions are put out of orientation with pre-defined angles.

15. A method according to claim 1, wherein:

the sighting directions are put out of orientation both by subjecting the detector heads to angulation and by providing their detection surface with an inclined collimator.

16. A method according to claim 1, wherein:

the examination is started by placing a bed in a substantially symmetrical position beneath the two detector heads.

17. A method according to claim 1, wherein:

a patient is raised without any lateral shift of the stand.

18. A method according to claim 1, wherein:

the stand is shifted in a circular motion about a patient on a bed without shifting the bed.

* * * * *